(12) United States Patent
Petersen et al.

(10) Patent No.: US 10,786,321 B2
(45) Date of Patent: Sep. 29, 2020

(54) INSTRUMENT FORCE SENSOR USING STRAIN GAUGES IN A FARADAY CAGE

(71) Applicant: Intuitive Surgical Operations, Inc., Sunnyvale, CA (US)

(72) Inventors: Alan W. Petersen, Cupertino, CA (US); Gerard J. Labonville, San Jose, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 67 days.

(21) Appl. No.: 16/072,140

(22) PCT Filed: Jan. 31, 2017

(86) PCT No.: PCT/US2017/015795
§ 371 (c)(1),
(2) Date: Jul. 23, 2018

(87) PCT Pub. No.: WO2017/136332
PCT Pub. Date: Aug. 10, 2017

(65) Prior Publication Data
US 2019/0069966 A1     Mar. 7, 2019

Related U.S. Application Data

(60) Provisional application No. 62/290,010, filed on Feb. 2, 2016.

(51) Int. Cl.
*G01D 7/00* (2006.01)
*A61B 34/00* (2016.01)
(Continued)

(52) U.S. Cl.
CPC .............. *A61B 34/71* (2016.02); *A61B 90/06* (2016.02); *A61B 2018/00595* (2013.01);
(Continued)

(58) Field of Classification Search
CPC .. B25J 15/0009; A61B 17/3462; A61B 34/37; A61B 34/76; A61B 2090/064;
(Continued)

(56) References Cited

U.S. PATENT DOCUMENTS 9,101,734 B2   8/2015  Selkee
9,186,797 B2   11/2015 Kim et al.
(Continued)

FOREIGN PATENT DOCUMENTS

EP          2644145 A1    10/2013
WO    WO-2015120108 A1    8/2015

OTHER PUBLICATIONS

International Preliminary Report on Patentability for Application No. PCT/US2017/015795, dated Aug. 16, 2018, 8 pages.
(Continued)

*Primary Examiner* — Brandi N Hopkins
(74) *Attorney, Agent, or Firm* — Schwegman Lundberg & Woessner, P.A.

(57) ABSTRACT

A surgical instrument includes a force sensor apparatus that is immune to noise from arcing cautery without relying on fiber optic strain gauges, and that is autoclavable. The surgical instrument includes a housing, a shaft, the force sensor apparatus, a joint, and an end component. The force sensor apparatus includes at least one strain gauge that is enclosed in a Faraday cage. The Faraday cage includes a sensor capsule that includes one or more strain gauges, a cable shield tube connected to the sensor capsule, and an electronics enclosure connected to the cable shield tube. The sensor capsule is positioned between the joint and the shaft. The cable shield tube extends through the shaft to the electronics enclosure that is within the housing.

14 Claims, 5 Drawing Sheets

(51) Int. Cl.
 *A61B 90/00* (2016.01)
 *A61B 18/00* (2006.01)
(52) U.S. Cl.
 CPC ... *A61B 2090/064* (2016.02); *A61B 2090/065* (2016.02); *A61B 2562/0261* (2013.01); *A61B 2562/12* (2013.01); *A61B 2562/182* (2013.01)
(58) Field of Classification Search
 CPC ... A61B 2034/305; A61B 34/71; A61B 34/35; A61B 34/30; A61B 2034/2061; A61B 2017/00477; A61B 90/06; A61M 25/00; G01L 1/246
 See application file for complete search history.

(56) References Cited

U.S. PATENT DOCUMENTS

| | | |
|---|---|---|
| 2007/0096666 A1 | 5/2007 | Ippisch |
| 2008/0065111 A1 | 3/2008 | Blumenkranz et al. |
| 2009/0095926 A1 | 4/2009 | MacNeish, III |
| 2010/0307265 A1 | 12/2010 | Werthschuetzky et al. |
| 2010/0313679 A1* | 12/2010 | Larkin ............... G01L 1/00 73/862.045 |
| 2010/0324453 A1 | 12/2010 | Lal et al. |
| 2013/0271159 A1 | 10/2013 | Santos et al. |
| 2013/0291654 A1* | 11/2013 | Blumenkranz ......... G01L 1/246 73/862.045 |
| 2014/0001236 A1* | 1/2014 | Shelton, IV ..... A61B 17/07207 227/176.1 |
| 2015/0075250 A1 | 3/2015 | Kosa et al. |
| 2015/0374449 A1* | 12/2015 | Chowaniec ...... A61B 17/07207 606/1 |

OTHER PUBLICATIONS

Extended European Search Report for Application No. 17748010 dated Aug. 28, 2019, 11 pages.
International Search Report and Written Opinion for Application No. PCT/US2017/015795, dated May 11, 2017, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

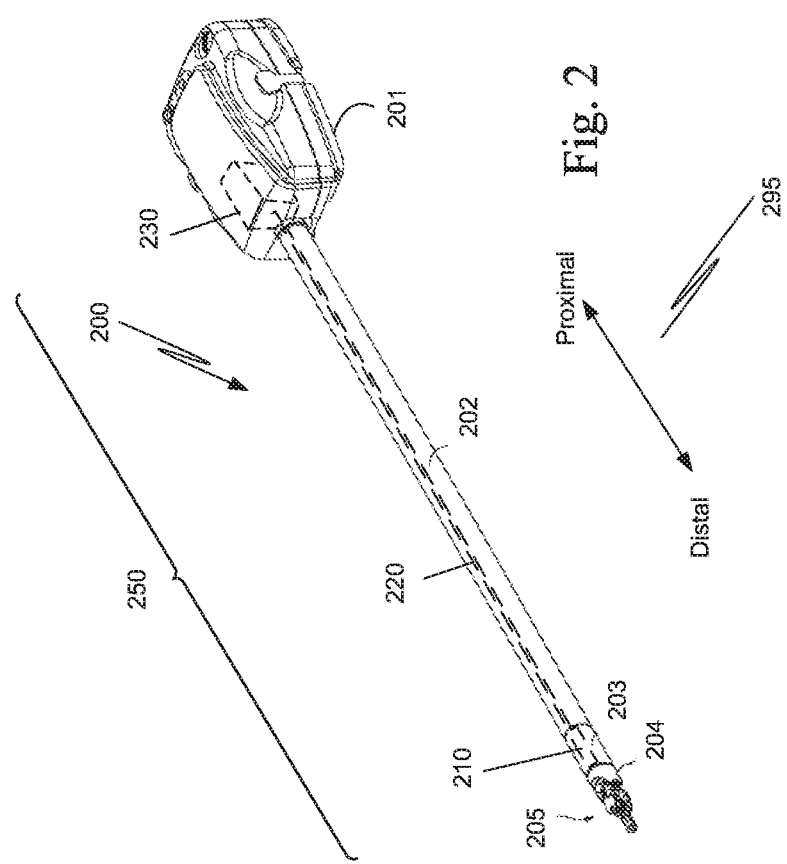

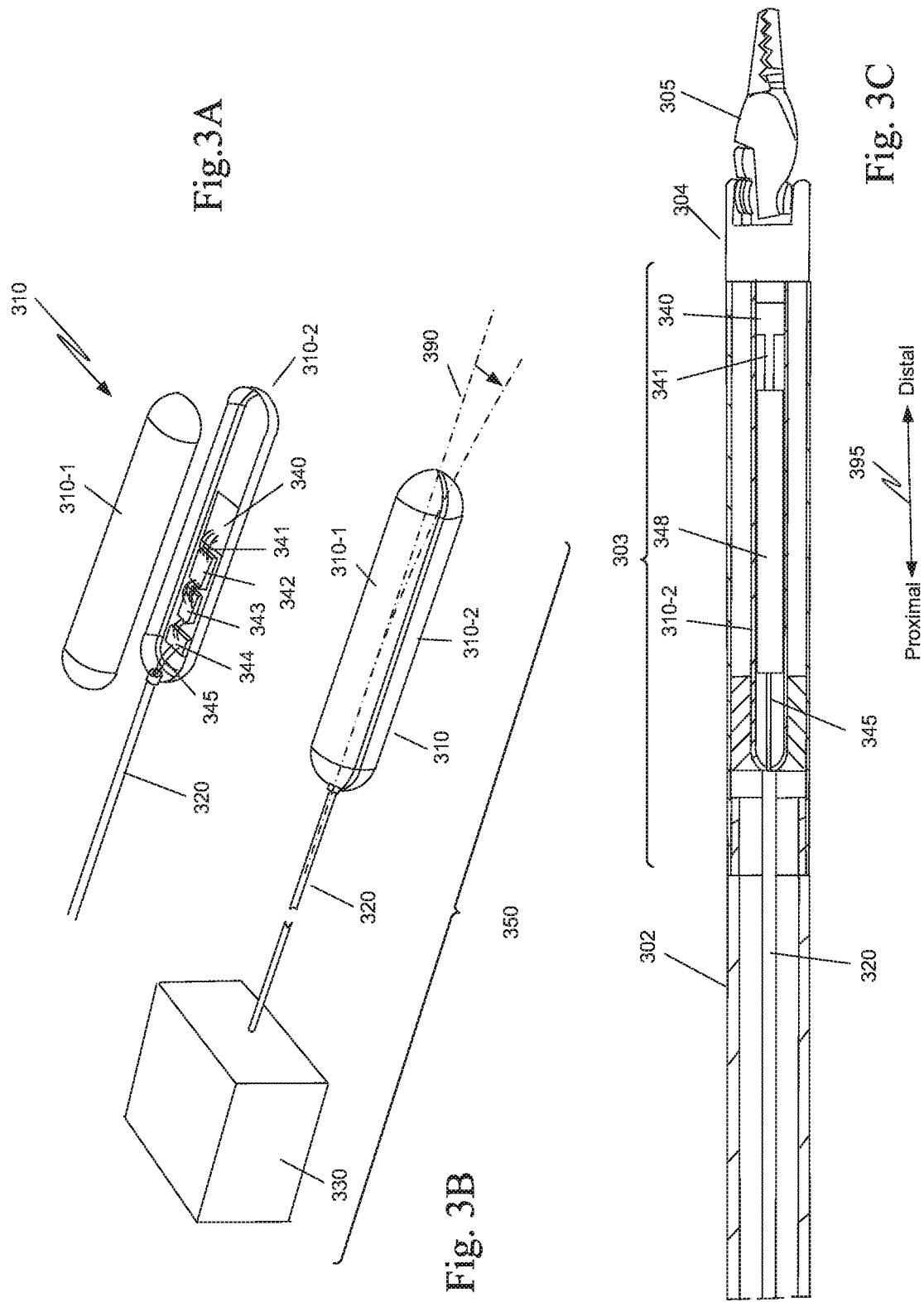

INSTRUMENT FORCE SENSOR USING STRAIN GAUGES IN A FARADAY CAGE

RELATED APPLICATIONS

This patent application is the U.S. national phase of International Patent Application No. PCT/US2017/015795, filed Jan. 31, 2017, which designated the U.S. and which claims priority to and the benefit of the filing date of U.S. Provisional Patent Application No. 62/290,010 (filed Feb. 2, 2016), each of which is incorporated by reference herein in its entirety.

BACKGROUND

Field of the Invention

The present invention relates generally to surgical instruments for computer-assisted surgical system, and more particularly to strain gauges used in surgical instruments for computer-assisted surgical systems.

Description of Related Art

FIG. 1 is a perspective illustration of a surgical instrument 100 used in a computer-assisted surgical system. Arrow 195 shows the proximal direction and the distal direction in FIG. 1.

Surgical instrument 100 includes a housing 101, a shaft 102, a force sensor apparatus 103, a joint 104, and an end component 105. End component 105, such as a surgical end effector, is coupled to force sensor apparatus 303 via joint 304, e.g., a wrist joint. Force sensor apparatus 103 is coupled to a distal end of a shaft 102 and is coupled to joint 104. Housing 101 is coupled to a proximal end of shaft 102, and housing 101 includes an interface which mechanically, electrically, and optically couples instrument 100 to an instrument manipulator assembly.

Force sensor apparatus 103 measured the flexing of instrument shaft 102 by forces acting on end component 105. Force sensor apparatus 103 used optical fibers including Fiber Bragg Gratings. Two rings of Fiber Bragg Gratings separated apart were used. Each ring included four Fiber Bragg Gratings separated by ninety degrees.

The signals from the Fiber Bragg Gratings were routed through the optical fibers to a fiber interrogator that was located remotely from surgical instrument 100. The signals from the fiber interrogator were combined arithmetically in various sums and differences to obtain measures of three perpendicular forces exerted on end component 105 and to obtain torques about two axes perpendicular to the axis of shaft 102. See U.S. Pat. No. 8,375,808 B2, which is incorporated herein by reference in its entirety, for a more complete description of the Fiber Bragg Grating sensors.

The Fiber Bragg Grating sensors reflect light based on the bending of the sensor. The Fiber Bragg Grating sensors were immune to cautery noise. Unfortunately, the epoxy glue used to attach the fibers to shaft 102 degrades when cleaned in an autoclave machine. This may result in a need to recalibrate the sensors, and also may limit the useful life of the surgical instrument with respect to force sensing if the epoxy glue fails.

SUMMARY

A surgical instrument includes a force sensor apparatus. The force sensor apparatus includes a sensor capsule. The sensor capsule is part of a Faraday cage. A strain gauge is mounted within the sensor capsule.

The surgical instrument also includes a tube and an electronics enclosure. The tube has a first end and a second end. The first end of the tube is connected to the sensor capsule. A second end of the tube is connected to the electronics enclosure. The tube and the electronics enclosure complete the Faraday cage. As used herein, a tube does not limited to having a circular cross section.

In one aspect, the sensor capsule is configured as a cantilever beam. The strain gauge is mounted on an interior wall of the cantilever beam. As used herein, a capsule does not imply only a closed body or any particular shape, for example, a capsule having an open end is disclosed.

In another aspect, the sensor capsule is a cylindrical tube. The cylindrical tube is mounted in the force sensor apparatus as a cantilever beam. In this aspect, the force sensor apparatus also includes a first plurality of strain gauges and a second plurality of strain gauges.

The cylindrical tube has an inner wall, a first end and a second end, and a lengthwise axis. The lengthwise axis is defined between the first end and the second end of the cylindrical tube. The first plurality of strain gauges is affixed to the inner wall of the cylindrical tube with a center of each gauge of the first set of strain gauges is in a first plane perpendicular to a first location on the lengthwise axis. The second plurality of strain gauges is affixed to the inner wall of the cylindrical tube, with a center of each gauge of the second set of strain gauges is in a second plane perpendicular to a second location on the lengthwise axis. The second location is different from the first location.

A first pair of strain gauges in the first plurality of strain gauges is configured in one leg (a first leg) of a Wheatstone Bridge. A first pair of strain gauges in the second plurality of strain gauges is configured in another leg (a second leg) of the Wheatstone Bridge.

The force sensor apparatus also includes an amplifier mounted within the cylindrical tube. The amplifier has a first input terminal, a second input terminal, and an output terminal. The first input terminal is connected to an output of the one leg (the first leg) of the Wheatstone Bridge. The second output terminal is connected to an output of the another leg (the second leg) of the Wheatstone Bridge. The amplifier is configured to subtract a signal on the second input terminal from a signal on the first input terminal, and is configured to provide on the output terminal a signal representative of a force acting on the cylindrical tube.

A force sensor apparatus includes a cantilever beam, a first plurality of strain gauges, a second plurality of strain gauges, and an amplifier circuit. The cantilever beam includes an interior wall, a first end, a second end, and a lengthwise axis. The interior wall bounds an interior volume. The lengthwise axis is defined between the first end and the second end of the cantilever beam. The cantilever beam is part of a Faraday cage.

The first plurality of strain gauges is mounted on the interior wall of the cantilever beam. A center of each gauge of the first plurality of strain gauges is in a first plane perpendicular to a first location on the lengthwise axis. The second plurality of strain gauges is also mounted on the interior wall of the cantilever beam. A center of each gauge of the second plurality of strain gauges is in a second plane perpendicular to a second location on the lengthwise axis of the cantilever beam. The second location is different from the first location.

The amplifier circuit is mounted in the interior volume of the cantilever beam. The amplifier circuit is connected to the first plurality of strain gauges and to the second plurality of strain gauges. The amplifier circuit is configured to output a first signal representative of a force in a first direction on the cantilever beam and to output a second signal representative of a force in a second direction on the cantilever beam. The first direction is perpendicular to the second direction.

In one aspect, a first pair of strain gauges in the first plurality of strain gauges is configured as one leg of a Wheatstone Bridge. A first pair of strain gauges in the second plurality of strain gauges is configured as another leg of the Wheatstone Bridge.

The amplifier circuit includes a first amplifier having a first input terminal, a second input terminal, and an output terminal. The first input terminal is connected to an output of the one leg of the Wheatstone Bridge. The second input terminal is connected to an output of the another leg of the Wheatstone Bridge. The amplifier is configured to subtract a signal on the second input terminal from a signal on the first input terminal, and is configured to provide on the output terminal the first signal representative of the force in the first direction on the cantilever beam.

In one aspect, a method includes mounting a strain gauge within a sensor capsule, and coupling the sensor capsule to a Faraday cage within a surgical instrument. The method also includes mounting the sensor capsule in the surgical instrument as a cantilever beam.

In one aspect, the mounting a strain gauge further includes mounting a first plurality of strain gauges on an interior wall of a cylindrical tube, the cylindrical tube being a part of the sensor capsule, and mounting a second plurality of strain gauges on the interior wall of the cylindrical tube. The first plurality of strain gauges is separated from the second plurality of strain gauges along a lengthwise axis of the cylindrical tube.

In this aspect, the method further includes configuring a pair of strain gauges in the first plurality of strain gauges as a first leg of a full Wheatstone Bridge, the full Wheatstone Bridge being within the cylindrical tube, and configuring a pair of strain gauges in the second plurality of strain gauges as a second leg of the full Wheatstone Bridge. An output of the first leg of the full Wheatstone Bridge is connected to a first input terminal of an amplifier and an output of the second leg of the full Wheatstone Bridge is connected to a second input terminal of the amplifier. The amplifier is within the cylindrical tube.

BRIEF DESCRIPTION OF THE DRAWINGS

FIG. 2 is a perspective illustration of a surgical instrument 200 that is used in a computer-assisted surgical system and that includes a force sensor apparatus that is immune to noise from arcing cautery and that is autoclabable.

FIGS. 3A to 3C are illustrations of one aspect of a Faraday cage that includes a sensor capsule, a tube, and an electronics enclosure that are included within a surgical instrument, such as the surgical instrument of FIG. 2.

Figure 1:
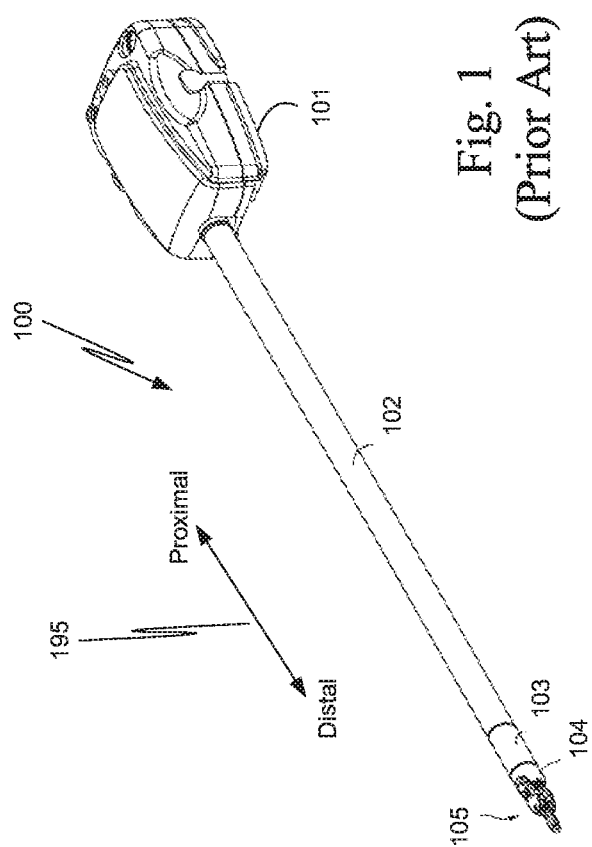
FIG. 1 is a perspective illustration of a prior art surgical instrument used in a computer-assisted surgical system.

In the drawings, the first digit of a three digit reference numeral is the figure number in which the element having that reference numeral first appeared.

DETAILED DESCRIPTION

A surgical instrument 200 includes a force sensor apparatus 203 that is immune to noise from arcing cautery without relying on fiber optic strain gauges and that is autoclabable. Surgical instrument 200 includes a housing 201, a shaft 202, a force sensor apparatus 203, a joint 204, and an end component 205. End component 205, such as a surgical end effector, is coupled to force sensor apparatus 203 via joint 204, e.g., a wrist joint. Force sensor apparatus 203 is coupled to a distal end of a shaft 202 and is coupled to joint 204. Housing 201 is coupled to a proximal end of shaft 202, and housing 201 includes an interface which mechanically and electrically couples instrument 200 to an instrument manipulator assembly. In FIG. 2, arrow 295 defines the proximal and distal directions.

As explained more completely below, force sensor apparatus 203 includes at least one strain gauge that is enclosed in a Faraday cage 250. Faraday cage 250 includes a sensor capsule 210 that includes one or more strain gauges, a tube 220, and an enclosure 230. In one aspect, each of sensor capsule 210, tube 220, and enclosure 230 is made of metal, e.g., stainless steel. While examples are presented herein of a capsule, these examples do not limit a capsule to only a closed body or to any particular shape. Also, as used herein, a tube is not limited to a tube having a circular cross section.

A first end of tube 220 is attached to sensor capsule 210 and a second end of tube 220 is attached to enclosure 230 so that any voltage or current on the exterior surface of Faraday cage 250 cannot penetrate inside Faraday cage 250.

Force sensor apparatus 203 includes one or more resistance strain gauges mounted on an inside wall, e.g., mounted in an interior volume, of sensor capsule 210. The resistance strain gauge or gauges sense the bending of sensor capsule 210, and so the resistance strain gauges measure torques on sensor capsule 210.

Amplifiers mounted in the interior volume of the sensor capsule 210 are connected to the resistance strain gauges. The amplifiers take signals from the resistance strain gauges and generate signals representative of forces acting on sensor capsule 210. These signal are driven on wires that run through an inner channel of tube 220 to circuits housed in enclosure 230 within housing 201. The electronics housed within enclosure 230 process the signals on the signal lines from the amplifiers.

Thus, the resistance strain gauges and the associated amplifiers that are included in sensor capsule 210 are immune from any common-mode voltages or currents induced by the arcing cautery, e.g., the reported resistance strain gauge data does not change when arcing cautery is present. Faraday cage 250 is important because the strain gauge signals are at the hundreds-of-microvolts level while cautery discharges are at the thousands-of-volts level. The arcing cautery interference is orders of magnitude larger than strain gauge signal levels.

Enclosures around the strain gauges, signal wires, and electronic circuits act not only as a Faraday cage, but also act as a sealed chamber preventing the steam and high pressures of the autoclave process from damaging the strain gauges and electronics. However, the strain gauges and the electronics are selected and built to survive the elevated temperature (140° C.) present during autoclave cleaning.

FIGS. 3A to 3C are illustrations of one aspect of a Faraday cage 350 that includes a sensor capsule 310, a tube 320, and an electronics enclosure 330 that are included within a surgical instrument, such as surgical instrument 200. Sensor capsule 310 includes a top portion 310-1, a lid, and a bottom portion 310-2, a base. In one aspect, top portion 310-1 and bottom half portion are each made of stainless steel.

Bottom portion 310-2 has a flat bottom and round sides. Strain gauge 340 and related circuitry 348 are mounted on the interior surface of the flat bottom of bottom portion 310-2.

Strain gauge 340, in this aspect, is a surface sputtered on the inner flat bottom surface of bottom portion 310-2. A first set of wires 341 connect strain gauge 340 to a Wheatstone Bridge amplifier 342, which in one aspect is a wire bonded integrated circuit. Wheatstone Bridge amplifier 342 is connected by a second set of wires to an analog-to-digital converter 343, which in one aspect also is a wire bonded integrated circuit. Analog-to-digital converter 343 is connected to an isolation and differential driver integrated circuit 344 by a third set of wires. A fourth set of wires, e.g., pair of wires 345, are connected to the output of differential driver integrated circuit 344 and routed through tube 320, a hypotube in one aspect. Tube 320 functions as a cable shield. In one aspect, Wheatstone Bridge amplifier 342, analog-to-digital converter 343, isolation and differential driver integrated circuit 344 are connected to each other by gold wire-bonding.

Tube 320, in one aspect, is a stainless steel hypotube that is laser welded to bottom portion 301-2 of sensor capsule 310. The proximal end of tube 320 is welded to a metallic enclosure 330 that is housed within the surgical instrument body. As shown in FIG. 3B, top portion 310-1 is laser welded to bottom portion 310-2 to form a sealed capsule that is sensor capsule 310. In this configuration, force sensor apparatus 303 measures a force that bends capsule 310 away from a lengthwise axis 390 of force sensor apparatus 303.

FIG. 3C is a cut-away view that shows force sensor apparatus 303 mounted on a distal end of shaft 302. Arrow 395 shows the proximal and distal directions in FIGS. 3A, 3B, and 3C. A wrist joint 304 and an end effector 305 are coupled to force sensor apparatus 303. Circuitry 348 represents Wheatstone Bridge amplifier 342, analog-to-digital converter 343, and isolation and differential driver integrated circuit 344. Capsule 310 is mounted as a cantilever beam in force sensor apparatus 303 to measure forces in one direction acting on end effector 305.

Figure 4A:
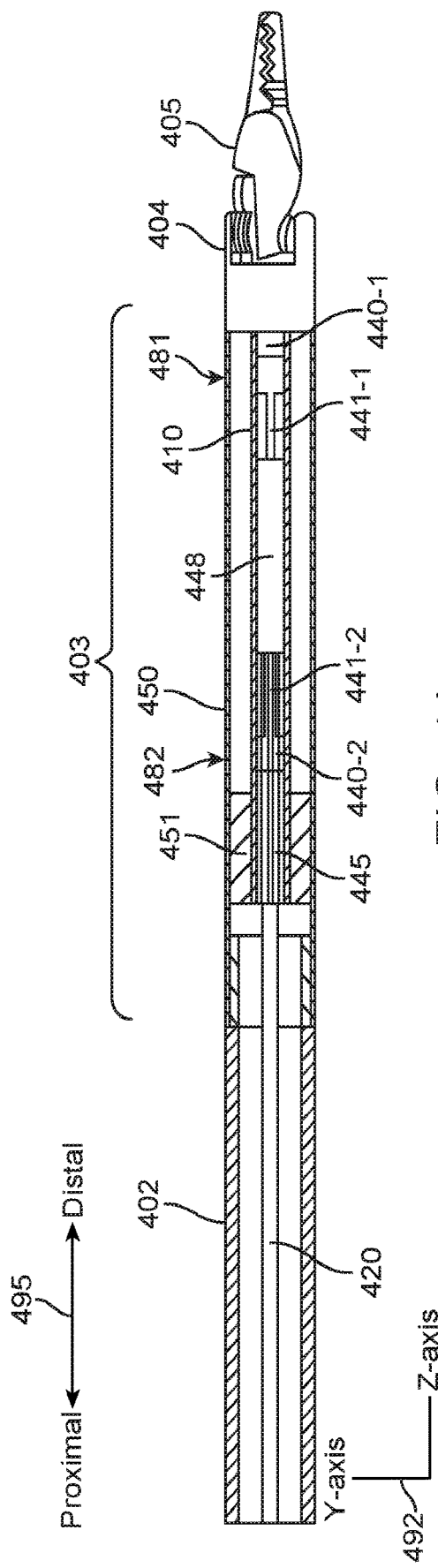
FIG. 4A is a cut-away view of another force sensor apparatus suitable for use in the surgical instrument of FIG. 2.

FIG. 4A is a cut-away view of another force sensor apparatus 403 suitable for use in surgical instrument 200. In FIG. 4A, force sensor apparatus 403 is mounted on a distal end of shaft 402. A wrist joint 404 is mounted on the distal end of force sensor apparatus 403, and an end component 405 is coupled to wrist joint 404.

The distal end of shaft 402 has a reduced outer diameter so that a first cylindrical tube 450 that is the outer wall of force sensor apparatus 403 slides over that reduced diameter. Arrow 495 defines the proximal and distal directions in FIG. 4A.

Sensor capsule 410 in force sensor apparatus 403 is a second cylindrical tube 410. The outer diameter of second cylindrical tube 410 is smaller than the inner diameter of first cylindrical tube 450, sometimes referred to as tube 450, so that second cylindrical tube 410 fits inside first cylindrical tube 450. In one aspect, tube 450 and tube 410 are each a metal tube, such as a stainless steel tube.

Second cylindrical tube 410, sometimes referred to as tube 410 or sensor capsule 410, is mounted inside first cylindrical tube 450 so that second cylindrical tube 410 functions a cantilever beam. Specifically, a proximal end portion of tube 410 is fixedly anchored in a proximal end of force sensor apparatus 403 by a rigid elongate bushing 451. The remaining portion of tube 410 is the cantilever beam, which extends from bushing 451 in the distal direction with the free distal end of tube 410 being inside the housing of wrist joint 404.

A metal plug is laser welded inside the distal end of tube 410. Alternatively the tube can be sealed with a water-proof adhesive such as a room temperature vulcanization silicone, commonly referred to as Silicone RTV. When Silicone RTV is used to seal the distal end of tube 410, a small non-metallic hole is left that has the size of the inner diameter of tube 410. However, cautery tests showed that for inner diameters of tubes used within a force sensor apparatus of a surgical instrument, the opening in the tube when sealed with Silicone RTV resulted in no cautery interference with the strain gauge data. Thus, the open-ended tube is an effective part of the Faraday cage. A distal end, a first end, of cable shield tube 420 extends through the proximal end of tube 410 and is welded or sealed with adhesive. A proximal end, a second end, of cable shield tube 420 is welded or sealed to an enclosure in the body of the surgical instrument, which is equivalent to enclosure 330. Thus, sensor capsule 410 and cable shield tube 420 are part of a Faraday cage.

For convenience, an X-Y-Z coordinate system is defined for FIG. 4A. The Z-axis is in a direction of the lengthwise axis of shaft 402 and force sensor apparatus 403. The Y-axis 492 is the up and down direction in FIG. 4A and the X-axis 491 (not shown) is into and out of the page. The Z direction of force sensor apparatus 403 is sometimes referred to as the lengthwise direction as opposed to a radial direction, the x-direction, and the y-direction. The proximal and distal directions are along the Z direction.

A first set of strain gauges includes a first plurality of strain gauges 440-1. First plurality of strain gauges 440-1 is mounted on an inner surface of tube 410 at a first location 481. A second set of strain gauges includes a second plurality of strain gauges 440-2. Second plurality of strain gauges 440-2 is mounted on the inner surface of tube 410 at a second location 482, which is a fixed distance in the lengthwise direction of force sensor apparatus 403 from first location 481 of first plurality of strain gauges 440-1.

A center of each of first plurality of strain gauges 440-1 is separated from a center of another of first plurality of strain gauges 440-1 by a fixed angle so that first plurality of strain gauges 440-1 are uniformly spaced around the inner diameter of tube 410. The result is a center of each of first plurality of strain gauges is in a first plane, which is perpendicular to first location 481 on the lengthwise axis.

Similarly, a center of each of the second plurality of strain gauges 440-2 is separated from a center of another of second plurality of strain gauges 440-2 by a fixed angle so that the second plurality of strain gauges is uniformly spaced around the inner diameter of tube 410. The result is a center of each of second plurality of strain gauges 440-2 is in a second plane, which is perpendicular to second location 482 on the lengthwise axis.

Figure 4B:
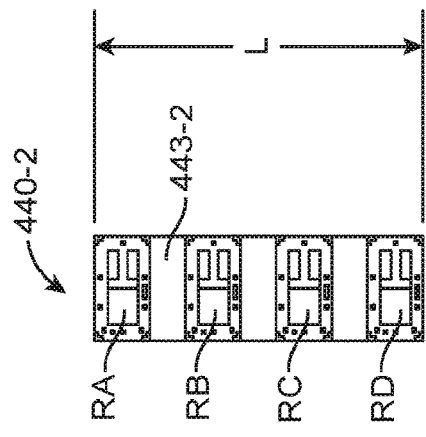
FIG. 4B is an illustration of a plurality of strain gauges, where the strain gauges are mounted in a row on a printed circuit assembly to form a strip used in the force sensor apparatus of FIG. 4A.
Figure 4C:
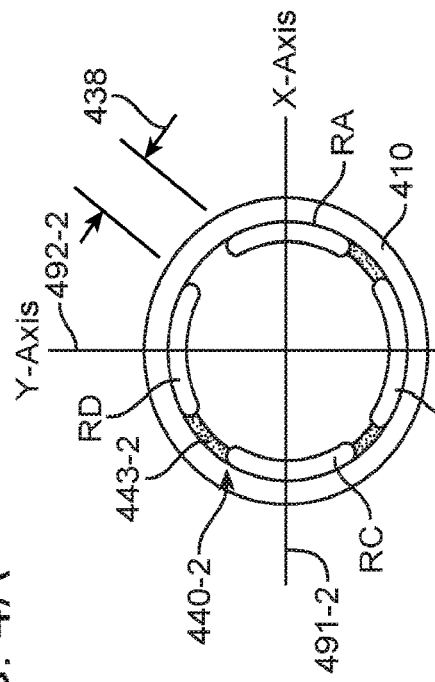
FIG. 4C is a cross-section view of the strip of FIG. 4B mounted in the cantilever beam of FIG. 4A.

In one aspect, the second plurality of strain gauges 440-2 includes four strain gauges, for example, see FIG. 4C, where second plurality of strain gauges 440-2 includes strain gauges RA, RB, RC, and RD that are uniformly spaced about the inner surface of tube 410. A center of each strain gauge is separated from the center of another strain gauge by a ninety degree angle. Also, the center of each of strain gauges RA, RB, RC, and RD is in an X-Y plane, which is perpendicular to the lengthwise axis of force sensor apparatus 403. (Herein and in the drawings, a bold reference numeral and a un-bolded reference numeral are the same reference numeral. Bolding is used only to help distinguish reference numerals from regular text in the description, and is not intended to distinguish between different elements.)

The strain gauges in first plurality of strain gauges 440-1 are similarly spaced as shown in FIG. 4C. See also, FIGS. 5C and 5D.

First plurality of strain gauges 440-1 is connected to strain gauge amplifiers 448 by first set of leads 441-1. Strain gauge amplifiers 448 are included within an interior volume of tube 410. The interior volume is bounded by the inner wall of tube 410. Second plurality of strain gauges 440-2 is connected to strain gauge amplifiers 448 by second set of leads 441-2.

Leads 445 connect strain gauge amplifiers 448 to electronics in the electronic enclosure in the body of the surgical instrument. Leads 445 pass though shield tube 420. In one aspect, leads 445 include five leads, a power lead, a ground lead, an X-axis force lead, a Y-axis force lead, and a temperature lead.

When a force is applied (perpendicularly to the lengthwise axis) anywhere along the distal end of sensor capsule 410, which, as just described, is the distal end of a cantilever beam, sensor capsule 410 bends. First and second pluralities of strain gauges 440-1, 440-2 inside tube 410 sense the strain on tube 410 at several locations to measure the bending stress on tube 410. The stress is a measure of the torque on tube 410 (or bending moment: caused by the length of the beam and the force applied). If the force is applied along tube 410 at a different location along its length (or if the length of tube 410 changes), the torque changes value. However, two pluralities of strain gauges 440-1, 440-2 are separated from each other along the length of tube 410, as illustrated in FIG. 4A, and measure the torque at each of the two locations. Algebraic subtracting of the measured torques yields a value for the force on tube 410, independent of where the force is applied along the length of the tube. This assumes that the force acting on the shaft is at location that is distal to the most distal set of strain gauges.

U.S. Pat. No. 8,375,808 B2, which was previously incorporated by reference, demonstrates that for strain gauges mounted on the outer surface of a tube, transverse forces can be measured independent of variations in the effective lever arm length and independent of changes in z-axis forces. While the derivation of the forces and torques in U.S. Pat. No. 8,375,808 B2 is for strain gauges located on the outside of a tube, the derivation is applicable to the strain gauges on the inner surface of the tube also, and so is not considered in further detail herein.

First plurality of strain gauges 440-1 measures the strain on the cantilever beam, i.e., tube 410, along the X and Y axes of shaft 402 at first location 481 on the Z-axis of the shaft 402. Second plurality of strain gauges 440-2 measures the strain on the cantilever beam, i.e., tube 410, along the X and Y axes of shaft 402 at second location 482 on the Z-axis of shaft 402, where the first location is different from the second location.

Two strain gauges in first plurality of strain gauges 440-1 that are located on the X-axis at first location 481 and two strain gauges in second plurality of strain gauges 440-2 that are located on the X-axis at second location 482 interconnected to form a full Wheatstone bridge arrangement. The output from the two X-axis strain gauges in first plurality of strain gauges 440-1 at first location 481 and the output from the two X-axis strain gauges in second plurality of strain gauges 440-2 at second location 482 go to an amplifier in strain gauge amplifiers 448, where the two outputs are subtracted and amplified, yielding the X-axis force on shaft 402. Herein, when it is said that a strain gauge is located on an axis, it means that the center of the strain gauge is positioned approximately on that axis, i.e., the center is on the axis to within manufacturing tolerances.

Similarly, two strain gauges in first plurality of strain gauges 440-1 that are located on the Y-axis at first location 481 and two strain gauges in second plurality of strain gauges 440-2 that are located on the Y-axis at second location 482 are interconnected to form a full Wheatstone bridge arrangement. The output from the two Y-axis strain gauges in first plurality of strain gauges 440-1 at first location 481 and the output from the two Y-axis strain gauges in second plurality of strain gauges 440-2 at second location 482 go to a second amplifier in strain gauge amplifiers 448, where the two outputs are subtracted and amplified, yielding a signal that represents the Y-axis force on shaft 402.

Hence, unlike prior configurations that output the torques to electronics in the housing of the surgical instrument or elsewhere in the surgical system to obtain the X-axis and Y-axis forces, force sensor apparatus 403 generates signals representing the X-axis and Y-axis forces directly, and so is said to generate the X-axis and Y-axis forces directly.

This has several advantages. It reduces the number of full Wheatstone Bridges that are required in force sensor apparatus 403. It reduces the number of leads that are required to carry signals off force sensor apparatus 403 and it reduces the number of amplifiers needed. It also eliminates the need for processor time to generate the forces from the measured torques. The reduction in the number of Wheatstone bridges, leads, and amplifiers required makes it feasible to implement force sensor apparatus 403 in a smaller volume, which is advantageous in a restricted volume such as that in the distal end of a surgical instrument shaft.

To facilitate mounting a set of strain gauges inside tube 410, in one aspect, the strain gauges are made as a strip of four strain gauges in a row. FIG. 4B is an illustration of second plurality of strain gauges 440-2, where strain gauges RA, RB, RC, and RD are mounted in a row on a printed circuit assembly to form strip 443-2, which in this example is a rectangular strip. First plurality of strain gauges 440-1 has the same configuration. See FIG. 5E.

Strain gauges RA, RB, RC, and RD are soldered to a printed circuit assembly and the result is referred to as strip 443-2. Strip 443-2 is curled into a cylinder to be placed inside tube 410. X-axis strain gauges and Y-axis strain gauges alternate on strip 443-2, so that when strip 443-2 is placed inside tube 410, the X-axis strain gauges are centered over the X-axis of tube 410 and the Y-axis strain gauges are centered over the Y-axis of tube 410. This quad design helps position the strain gauges at the correct spot on the tube's inside surface.

A length L of strip 443-2 is made as small as possible, leaving a gap 438 between the two ends of strip 443-2 when strip 443-2 is mounted within tube 410, as illustrated in FIG. 4C. The purpose of gap 438 is to allow strip 443-2 to be curled-up tighter (with no gap) during insertion, making the curled strip diameter smaller than the tube inside diameter. The outer surface of curled strip 443-2 is tacky with adhesive and requires a reduced diameter during insertion into the tube. Thus, length L of strip 443-2 is smaller than an inner circumference of the inner surface of tube 410.

Figure 5A:
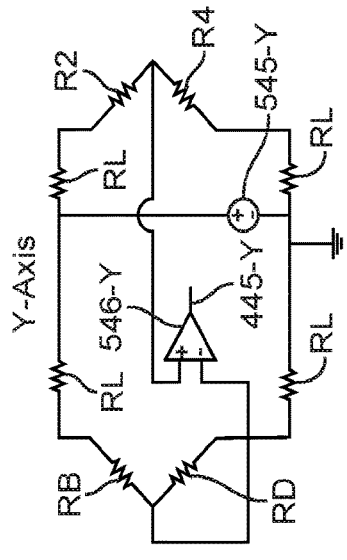
FIGS. 5A and 5B are schematics of Wheatstone Bridges and amplifiers used to generate signals representative of the forces on the cantilever beam of FIG. 4A.
Figure 5C:
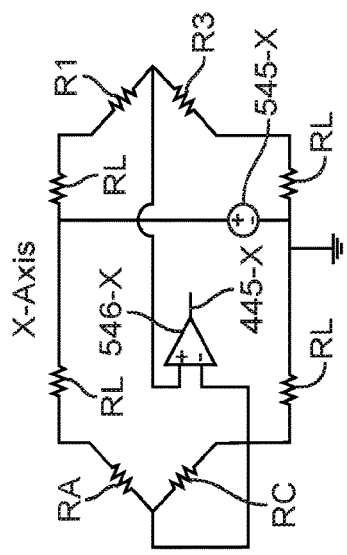
FIGS. 5C and 5D illustrate the orientation of the strain gauges in force sensor apparatus of FIG. 4A.
Figure 5B:
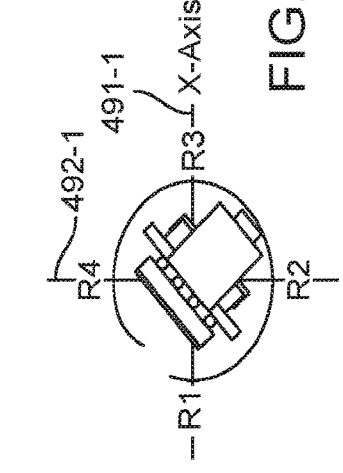
Figure 5D:
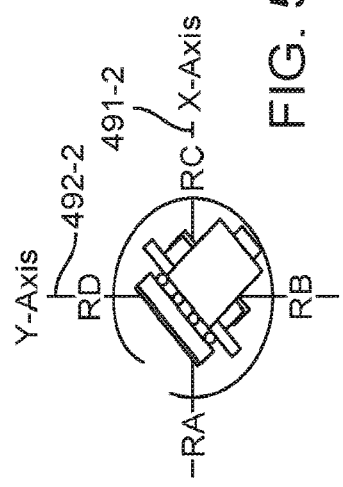
Figure 5E:
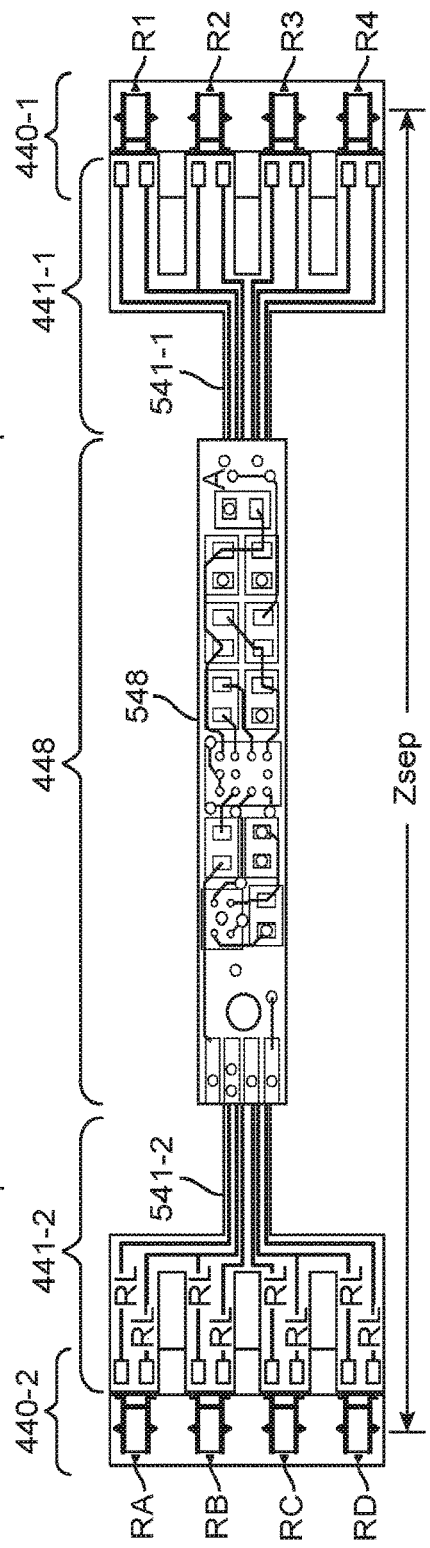
FIG. 5E is an illustration of the strain gauge and amplifier configuration that is inserted within the cantilever beam of FIG. 4A.

FIGS. 5A and 5B are schematics of Wheatstone Bridges and amplifiers used to generate signals representative of the forces on cantilever beam-type second cylindrical tube 410. FIGS. 5C and 5D illustrate the orientation of the strain gauges in force sensor apparatus 403. FIG. 5E is an illustration of the strain gauge and amplifier configuration that is inserted within tube 410.

A center of each of X-axis strain gauges R1 and R3 in first plurality of strain gauges 440-1 (FIG. 5D) is located on X-axis 491-1 in a plane, which extends through first location 481 along the lengthwise axis of shaft 402. A center of each of strain gauges RA and RC in second plurality of strain gauges 440-2 (FIG. 5C) is located on X-axis 491-2, in a plane, which extends through second location 482.

Strain gauges R1 and R3 and strain gauges RA and RC are connected to form a full X-axis Wheatstone bridge as illustrated in FIG. 5A. Resister RL is the resistance of a lead RL in FIG. 5E. (In FIGS. 5A and 5B, the same reference numeral is used for an element as for the resistance of that element.) A bridge excitation voltage supply 545-X powers the two sets of strain gauges in the full X-axis Wheatstone Bridge.

X-axis strain gauges R1 and R3 form a first leg of the full X-axis Wheatstone Bridge. The output from X-axis strain gauges R1 and R3 is a first input to a first amplifier 546-X. X-axis strain gauges RA and RC form a second leg of the full X-axis Wheatstone Bridge. The output from X-axis strain gauges RA and RC is a second input to amplifier 546-X of strain gauge amplifiers 448. Amplifier 546-X subtracts outputs from the two legs of the Wheatstone Bridge and drives a signal on X-axis force output line 445-X that represents the X-axis force on shaft 402.

Similarly, a center of each of Y-axis strain gauges R2 and R4 in first plurality of strain gauges 440-1 (FIG. 5D) is located on Y-axis 491-1 in the plane, which extends through first location 481 along the lengthwise axis of shaft 402. A center of each of strain gauges RB and RD in second plurality of strain gauges 440-2 (FIG. 5C) is located on X-axis 491-2 in the plane, which extends through second location 482.

Strain gauges R2 and R4 and strain gauges RB and RD are connected to form a full Y-axis Wheatstone bridge as illustrated in FIG. 5B. Strain gauges R2 and R4 form a first leg of the full Y-axis Wheatstone bridge, and strain gauges RB and RD form a second leg of the full Y-axis Wheatstone bridge. Resister RL is the resistance of a lead RL in FIG. 5E.

A bridge excitation voltage supply 545-Y powers the two sets of strain gauges in the full Y-axis Wheatstone bridge. The output from Y-axis strain gauges R2 and R4 is a first input to a second amplifier 546-Y and the output from Y-axis strain gauges RB and RD is a second input to amplifier 546-Y of strain gauge amplifiers 448.

Amplifier 546-Y subtracts two outputs and drives a signal on Y-axis force output line 445-Y that represents the Y-axis force on shaft 402. In one aspect, bridge excitation voltage supply 545-Y and bridge excitation voltage supply 545-X are a common power supply.

As described above, strain gauges R1, R2, R3, and R4 are soldered to a first printed circuit assembly, i.e., surface mounted on the printed circuit assembly, to form a first plurality of strain gauges 440-1 (FIG. 5E). Strain gauges RA, RB, RC, and RD are soldered to a second printed circuit assembly to form a second plurality of strain gauges 440-2. In one aspect, each of strain gauges R1, R2, R3, R4, RA, RB, RC, and RD is a high-temperature-rated, instrument-grade strain gauge made of Karma material so that the zero-load output drifts minimally vs. autoclave cycles.

Strain gauge amplifiers 448 do not include any analog-to-digital converter integrated circuits or any differential driver integrated circuits. These integrated circuits are included in the electronics within the Faraday cage enclosure in the surgical instrument body. Strain gauge amplifiers 448 are mounted on a rigid printed circuit board 548. A first integral flex circuit 541-1 connects rigid printed circuit board 548 to first plurality of strain gauges 440-1. A second integral flex circuit 541-2 connects rigid printed circuit board 548 to second plurality of strain gauges 440-2. A center of first plurality of strain gauges 440-1 is separated from a center of second plurality of strain gauges by a lengthwise distance Zsep, which in one aspect is 34 mm.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

We claim:

1. A surgical instrument comprising:
 a force sensor apparatus comprising:
  a sensor capsule, the sensor capsule being part of a Faraday cage, the sensor capsule being mounted in the force sensor as a cantilever beam, the sensor capsule including top portion and a bottom portion having a flat bottom; and
  a strain gauge mounted within the sensor capsule to an interior surface of the flat bottom of the bottom portion.

2. The surgical instrument of claim 1 further comprising:
 a tube having a first end and a second end, the first end being connected to the sensor capsule, the tube being part of the Faraday cage.

3. The surgical instrument of claim 2, further comprising:
 an electronics enclosure connected to the second end of the tube, the electronics enclosure being part of the Faraday cage.

4. A surgical instrument comprising:
 a force sensor apparatus comprising a sensor capsule and a strain gauge mounted within the sensor capsule,
  the sensor capsule being part of a Faraday cage,
  the sensor capsule comprising a cylindrical tube,
  the cylindrical tube being mounted in the force sensor apparatus as a cantilever beam,
  the cylindrical tube having an inner wall, a first end, a second end, and a lengthwise axis defined between the first end and the second end;
 a first plurality of strain gauges and a second plurality of strain gauges, wherein the strain gauge is a strain gauge within one of the first plurality of strain gauges and the second plurality of strain gauges;
 the first plurality of strain gauges being affixed to the inner wall of the cylindrical tube with a center of each gauge of the first plurality of strain gauges being in a first plane perpendicular to a first location on the lengthwise axis; and
 the second plurality of strain gauges being affixed to the inner wall of the cylindrical tube, with a center of each gauge of the second plurality of strain gauges being in a second plane perpendicular to a second location on the lengthwise axis.

5. The surgical instrument of claim 4:
 a first pair of strain gauges in the first plurality of strain gauges being configured as a first leg of a Wheatstone Bridge; and
 a first pair of strain gauges in the second plurality of strain gauges being configured as a second leg of the Wheatstone Bridge.

6. The surgical instrument of claim 5, the force sensor apparatus further comprising:
 an amplifier mounted within the cylindrical tube, the amplifier having a first input terminal, a second input terminal, and an output terminal;
 the first input terminal being connected to an output of the first leg of Wheatstone Bridge;
 the second input terminal being connected to an output of the second leg of the Wheatstone Bridge; and
 the amplifier being configured to subtract a second signal on the second input terminal from a first signal on the first input terminal, and being configured to provide on the output terminal an output signal representative of a force acting on the cylindrical tube.

7. A force sensor apparatus comprising:
 a cantilever beam having an interior wall, a first end, a second end, and a lengthwise axis, the interior wall bounding an interior volume, the lengthwise axis being defined between the first end and the second end;
 a first plurality of strain gauges mounted on the interior wall, a center of each of the first plurality of strain gauges being in a first plane perpendicular to a first location on the lengthwise axis;
 a second plurality of strain gauges mounted on the interior wall, a center of each of the second plurality of strain gauges being in a second plane perpendicular to a second location on the lengthwise axis, the second location being different from the first location; and
 an amplifier circuit mounted in the interior volume, the amplifier circuit being connected to the first plurality of strain gauges and to the second plurality of strain gauges, the amplifier circuit being configured to output a first signal representative of a force in a first direction on the cantilever beam and to output a second signal representative of a force in a second direction on the cantilever beam, the first direction being perpendicular to the second direction.

8. The force sensor apparatus of claim 7:
 a first pair of strain gauges in the first plurality of strain gauges being configured as one leg of a Wheatstone Bridge; and
 a first pair of strain gauges in the second plurality of strain gauges being configured as another leg of the Wheatstone Bridge.

9. The force sensor apparatus of claim 8; the amplifier circuit further comprising:
 a first amplifier having a first input terminal, a second input terminal, and an output terminal;
 the first input terminal being connected to an output of the one leg of the Wheatstone Bridge;
 the second input terminal being connected to an output of the another leg of the Wheatstone Bridge; and
 the first amplifier being configured to subtract a signal on the second input terminal from a signal on the first input terminal, and being configured to provide on the output terminal the first signal representative of the force in the first direction on the cantilever beam.

10. The force sensor apparatus of claim 7, the cantilever beam being part of a Faraday cage.

11. A method comprising:
 mounting a first strain gauge of a first plurality of strain gauges onto an interior wall of a cylindrical tube of a sensor capsule; and
 coupling the sensor capsule as a cantilever beam, within the surgical instrument, to a Faraday cage within a surgical instrument.

12. The method of claim 11, further comprising:

mounting a second plurality of strain gauges on the interior wall of the cylindrical tube, the first plurality of strain gauges being separated from the second plurality of strain gauges along a lengthwise axis of the cylindrical tube.

13. A method comprising:

coupling a sensor capsule, with at least one strain gauge located therein, to a Faraday cage within a surgical instrument;

mounting the sensor capsule in the surgical instrument as a cantilever beam;

mounting a first plurality of strain gauges on an interior wall of a cylindrical tube, the cylindrical tube being a part of the sensor capsule;

mounting a second plurality of strain gauges on the interior wall of the cylindrical tube, the first plurality of strain gauges being separated from the second plurality of strain gauges along a lengthwise axis of the cylindrical tube;

configuring a pair of strain gauges in the first plurality of strain gauges as a first leg of a full Wheatstone Bridge, the full Wheatstone Bridge being within the cylindrical tube; and configuring a pair of strain gauges in the second plurality of strain gauges as a second leg of the full Wheatstone Bridge.

14. The method of claim 13, further comprising:

connecting an output of the first leg of the full Wheatstone Bridge to a first input terminal of an amplifier; and connecting an output of the second leg of the full Wheatstone Bridge to a second input terminal of the amplifier, the amplifier being within the cylindrical tube.

\* \* \* \* \*

UNITED STATES PATENT AND TRADEMARK OFFICE
CERTIFICATE OF CORRECTION

PATENT NO. : 10,786,321 B2
APPLICATION NO. : 16/072140
DATED : September 29, 2020
INVENTOR(S) : Petersen et al.

Page 1 of 1

It is certified that error appears in the above-identified patent and that said Letters Patent is hereby corrected as shown below:

In the Claims

In Column 11, Line 25, in Claim 1, after "including", insert --a--

In Column 11, Line 38, in Claim 4, after "and", delete "¶"

In Column 11, Line 61, in Claim 5, delete "claim 4:" and insert --claim 4 further comprising:-- therefor In Column 12, Line 7, in Claim 6, after "of", insert --the--

In Column 12, Line 39, in Claim 8, delete "claim 7:" and insert --claim 7 further comprising:-- therefor In Column 12, Line 46, in Claim 9, delete "claim 8;" and insert --claim 8,-- therefor Signed and Sealed this
First Day of December, 2020

Andrei Iancu
*Director of the United States Patent and Trademark Office*